US009702842B2

(12) United States Patent
Hong et al.

(10) Patent No.: US 9,702,842 B2
(45) Date of Patent: Jul. 11, 2017

(54) AMPEROMETRIC SENSORS AND DEVICES FOR MEASURING CONCENTRATION OF S-NITROSOTHIOLS BASED ON PHOTO-INDUCED DECOMPOSITION OF S-NITROSOTHIOLS

(75) Inventors: Sung A Hong, Seoul (KR); Da Yeon Sung, Seoul (KR); Jun Hee Han, Seoul (KR); Jea Hun Song, Seoul (KR); Hakhyun Nam, Seoul (KR); Geun Sig Cha, Seoul (KR); Jae Ho Shin, Seoul (KR)

(73) Assignee: I-SENS, INC., Seoul (KR)

( * ) Notice: Subject to any disclaimer, the term of this patent is extended or adjusted under 35 U.S.C. 154(b) by 80 days.

(21) Appl. No.: 13/264,382

(22) PCT Filed: Apr. 14, 2011

(86) PCT No.: PCT/KR2011/002688
§ 371 (c)(1),
(2), (4) Date: Oct. 13, 2011

(87) PCT Pub. No.: WO2012/133974
PCT Pub. Date: Oct. 4, 2012

(65) Prior Publication Data
US 2014/0014512 A1  Jan. 16, 2014

(30) Foreign Application Priority Data

Mar. 30, 2011 (KR) .................. 10-2011-0028575
Apr. 14, 2011 (KR) .................. 10-2011-0034662

(51) Int. Cl.
*G01N 27/30*    (2006.01)
*G01N 27/327*   (2006.01)

(52) U.S. Cl.
CPC ......... *G01N 27/30* (2013.01); *G01N 27/3271* (2013.01)

(58) Field of Classification Search
CPC ............... G01N 27/30; G01N 27/3271; G01N 21/7703; G01N 2021/772;
(Continued)

(56) References Cited

U.S. PATENT DOCUMENTS

2006/0084097 A1   4/2006  Hu et al.
2008/0176271 A1   7/2008  Silver et al.
(Continued)

OTHER PUBLICATIONS

David J. Welker and Jeff Tostenrude, Fabrication and characterization of a single mode electro-optic polymer optical fiber, Optics Letters, vol. 23, No. 23, pp. 1826-1828 (1998).*
(Continued)

*Primary Examiner* — Luan Van
*Assistant Examiner* — Maris R Kessel
(74) *Attorney, Agent, or Firm* — Masuvalley & Partners

(57) ABSTRACT

Provided are an amperometric sensor and device for electrochemically quantifying nitrosothiol (RSNO), which is associated with storage and delivery of nitric oxide (NO) in the human body. The amperometric sensor for measuring a concentration of RSNO includes an electrode configured to measure an electric current generated by an oxidation reaction of NO, and a means configured to start and stop photo-induced decomposition of RSNO. Here, the electric current is measured by the oxidation reaction of NO before and after the photo-induced decomposition of RSNO. The amperometric sensor may measure separate signals of RSNO and NO, which are present in the sample at the same time, using one electrode, thereby preventing an inhibition action caused by NO during the measurement of RSNO. Also, the amperometric sensor is simple in structure and easy to manufacture and may be applied to manufacture of a small electrode, and thus may be developed as a sensor for in vivo measurements.

14 Claims, 13 Drawing Sheets

(58) Field of Classification Search
CPC .......... G01N 2021/7786; A61B 5/1459; A61B 5/14532; C12G 1/006
USPC .... 204/400, 403.01, 403.04, 403.05, 403.06; 205/775, 777.5, 778, 792, 793
See application file for complete search history.

(56) References Cited

U.S. PATENT DOCUMENTS

| | | |
|---|---|---|
| 2009/0017552 A1 | 1/2009 | Lippard et al. |
| 2009/0029390 A1 | 1/2009 | Yang et al. |
| 2009/0112193 A1* | 4/2009 | Hyde et al. ............. 606/11 |

OTHER PUBLICATIONS

C.R. Zamarreno, M. Hernaez, I. Del Villar, I.R. Matias, F. J. Arregui, Tunable humidity sensor based on ITO-coated optical fiber, Sensor and Actuators B, 146, p. 414-417 (2010).*

Susan L. R. Barker, Yunde Zhao, Michael A. Marietta, and Raoul Kopelman, Cellular Applications of Sensitive and Selective Fiber-Optic Nitric Oxide Biosensor based on a Dye-Label Heme Domain of Solulble Guanylate, Anal. Chem., 71, pp. 2071-2075 (1999).*

S. Khan et al., A fluorescence-based imaging-fiber electrode chemical sesnor for hydrogen peroxide, Analytica Chimica Acta., vol. 404, pp. 213-221 (2000).*

I. Biran, et al., Chapter 1: Optrode-Based Fiber Optic Biosesnors (Bio-Optrode), Optical Biosensors: Today and Tomorrow (2nd Edition), pp. 3-82 (2008).*

J.H. Shin et al., Fluorinated Xerogel-Derived Microelectrode for Amperometric Nitric Oxide Sensing, Anal. Chem., vol. 80, issue 18, pp. 6850-6859 (2008).*

Radomski, M.W. et al., "An L-arginine/nitric oxide pathway present in human platelets regulates aggregation." Proc. Natl. Acad. Sci. USA vol. 87, pp. 5193-5197, Jul. 1990.

Langrehr, J.M. et al., "Nitric Oxide—A New Endogenous Immunomodulator." Transplantation vol. 55, pp. 1205-1212, No. 6, Jun. 1993.

Ohta, A. et al., "Localization of nitric oxide synthase-immunoreactive neurons in the solitary nucleus and ventrolateral medulla oblongata of the rat: their relation to catecholaminergic neurons." Neuroscience Letters, 158 (1993) pp. 33-35.

Cha, W.S. et al., "Catalytic generation of nitric oxide from S-nitrosothiols using immobilized organoselenium species." Biomaterials 28 (2007) pp. 19-27.

Zhang, Y. et al., "The mechanism of transmembrane S-nitrosothiol transport." Proc. Natl. Acad. Sci. USA, 2004, 101, pp. 7891-7896.

Williams, D.L.H., "The Chemistry of S-Nitrosothiols." Acc. Chem. Res. 1999, 32, pp. 869-876.

Cha, W. et al., "Amperometric S-nitrosothiol sensor with enhanced sensitivity based on organoselenium catalysts." Biosensors and Bioelectronics 24 (2009) pp. 2441-2446.

Da Yeon Sung et al., "Abstract—Electrochemistry: Method Development and Applications", Amperometric Sensing of S-nitrosothiols Based on Their Photo-induced Decomposition: Optically Switchable Determination Nitric Oxide and S-nitrosothiols, Mar. 15, 2011, 2011 Pittcon Conference.

* cited by examiner

AMPEROMETRIC SENSORS AND DEVICES FOR MEASURING CONCENTRATION OF S-NITROSOTHIOLS BASED ON PHOTO-INDUCED DECOMPOSITION OF S-NITROSOTHIOLS

CLAIM OF PRIORITY

This application claims priority to and the benefit of Korean Patent Application Nos. 2011-28575 filed on Mar. 30, 2011 and 2011-34662 filed on Apr. 14, 2011 the disclosure of which is incorporated herein by reference in its entirety.

FIELD

The present invention relates to an amperometric sensor and device for measuring a concentration of nitrosothiol (RSNO), and more particularly, to a means capable of measuring separate signals from nitric oxide (NO) and RSNO when present in a sample at the same time, using one electrode, using the fact that nitrosothiol tends to be optically decomposed when two materials are present in a sample at the same time. That is, the present invention relates to a means capable of reliably measuring RSNO using a simple and easy method by excluding an inhibition action caused by NO during the measurement of a concentration of RSNO.

BACKGROUND ART

Functions of nitric oxide (NO) in the cardiovascular system, respiratory system, digestive system, urinary system and nervous system have been elucidated in the fields of biochemistry and physiology, and thus research on NO has been increasingly conducted. The vasodilation and anti-thrombosis characteristics of NO (Radomski, M. W et al., Proc. Natl. Acad. Sci. U.S.A. 1990, 87, 5193-5197) have been applied to development of drugs in the cardiovascular system, and the phagocytosis of NO with which macrophages are associated has been applied to development of a tumoricidal agent (Langrehr, J. M et al., Transplantation 1993, 55, 1205-1212), an antibiotic and a bactericidal agent. Also, NO is an intercellular signaling molecule (Ohta, A. et al Neurosci. Lett. 1993, 158, 33-35). In order to investigate a specific reaction mechanism of NO, it is very important to directly measure NO in the human body or in the inside or outside of cells producing NO.

Meanwhile, researchers have started to display interest in storage or delivery of NO in the human body as physiological and medical roles of NO become important. In particular, researchers have taken a great interest in that NO, which is a radical molecule having high reactivity, shows stable physiological activities due to its short life span (Cha, W. S. et al., Biomaterials 2007, 28(1), 19-27). RSNO is a solution to such a problem. That is, NO is modified into RSNO in cells for its delivery (Zhang, Y. et al., Proc. Natl. Acad. Sci. USA, 2004, 101, 7891-7896).

In recent years, much research has been conducted to measure a concentration of RSNO associated with the storage and delivery of NO.

RSNO is represented by the following Formula 1, and is formed by nitrosylating a sulfhydryl group (R-SH) with NO. Also, physical/chemical properties of RSNO decomposed by color or light are different according to functional groups R, and may play various roles or be present in various positions when RSNO is present as an in vivo molecule.

Formula 1

FIG. 1 shows representative RSNO compounds present in a living body (Williams D. L-H. et al., Acc. Chem. Res. 1999, 32, 869-876). Unlike conventional RSNO compounds which are unstable in the air, there are a limited number of RSNO compounds which are stable in the air.

The biochemical activities of RSNO are realized by generation of NO caused by the breakdown of an S—N bond. FIG. 2 shows a mechanism in which NO is produced from RSNO. FIGS. 2A and 2B show decomposition caused by a metal catalyst, Cu ((I) and (II)), FIG. 2C shows photo-induced decomposition caused by light, and FIG. 2D show decomposition caused by cross nitrosation.

RSNO is present at a low concentration from several nM to several μM in a living body, and present at different amounts according to body regions. Therefore, a sensor has to show very high sensitivity to measure RSNO. Also, since RSNO tends to be unstably and easily decomposed in the air, a sensor should meet requirements such as being able to desirably measure RSNO in a living body and having enhanced selectivity to RSNO among numerous nuisance species present in the living body.

A conventional method of measuring RSNO includes a method using an electrochemical NO sensor. That is, RSNO is indirectly quantified by decomposing RNSO using Cu ((I) and (II)) or a biochemical catalyst as the metal catalyst and measuring generated NO using an electrochemical NO sensor. However, such a method has a problem in that, when RSNO and NO are present together in a sample, the sensor does not differentiate the existing NO from NO generated by decomposition of RSNO using the catalyst. In other words, during measurement of RSNO, NO acts as a nuisance species. Therefore, it is impossible to measure a precise concentration of RSNO in a living body using the above-described method.

In order to solve such a problem, an attempt has been made to constitute a differential electrode system (Cha, W. et al., Biosens. Bioelectron. 2009, 24, 2441-2446) for correction. That is, this is a method of measuring a concentration of RSNO using two working electrodes, which includes measuring concentrations RSNO and NO together using one working electrode, measuring only a concentration of NO using the other working electrode and calculating a difference value between sensor signals obtained from the two working electrodes. However, such a method has problems in that the sensitivity to NO should be precisely the same in the two working electrodes, and a measurement device is complicated and larger in scale due to the use of the two working electrodes, which makes it difficult to perform direct measurements in the living body.

SUMMARY

In order to solve the above-mentioned problems, the present invention is directed to providing an amperometric sensor for measuring a concentration of RSNO, which is able to reliably measure a concentration of RSNO by excluding an inhibition action caused by the presence of NO during the measurement of RSNO.

Also, the present invention is directed to providing a small amperometric sensor which is easy to manufacture and simple in structure since the amperometric sensor may differentiate signals of RSNO and NO from each other, which makes it possible to apply to human bodies.

Also, the present invention is directed to providing an amperometric sensor for measuring a concentration of RSNO. Here, the amperometric sensor includes an electrode configured to measure an electric current generated by an oxidation reaction of NO and a means configured to start and stop photo-induced decomposition of RSNO. Here, the electric current is measured by the oxidation reaction of NO before and after the photo-induced decomposition of RSNO.

The means configured to start and stop the photo-induced decomposition of RSNO may be a photocatalyst switch configured to introduce the electrode into an optical fiber, mount a light source on the optical fiber into which electrode is introduced and control interception and supply of light from the light source to the optical fiber.

The electrode may be introduced into the optical fiber by depositing one material selected from the group consisting of platinum, gold, silver, vanadium, niobium, tantalum, indium, titanium, nickel, molybdenum, iron, copper, cobalt, chromium, bismuth, aluminum, nickel chromium and a combination thereof on an end surface of the optical fiber.

The electrode may be introduced into the optical fiber by manufacturing one material selected from the group consisting of platinum, gold, silver, vanadium, silicon oxide, niobium, tantalum, indium, titanium, nickel, molybdenum, iron, copper, cobalt, chromium, graphite, bismuth, aluminum, zinc oxide manganese, nickel chromium and a combination thereof in a wire, rod or plate shape and attaching the material in the wire, rod or plate shape to the optical fiber.

The electrode may be introduced into the optical fiber by coating a mixed composition, which includes a paraffinic oil and at least one material selected from the group consisting of gold, carbon, silver, platinum and a mixture of silver and carbon, on an end surface of the optical fiber.

The electrode may be formed by coating a mixed composition, which includes a paraffinic oil and at least one material selected from the group consisting of gold, carbon, silver, platinum and a mixture of silver and carbon, on an end surface of a cylindrical optical fiber, an operating circuit connection line may be mounted on a lateral surface of the optical fiber, and a coating layer from the mixed composition may be formed on a lateral surface of the optical fiber including the operating circuit connection line.

A coating of an insulating material may be further provided over the coating layer formed on the lateral surface of the optical fiber.

The optical fiber may be in a cylindrical shape having a diameter of 250 μm to 3 mm, and be made of plastic, silica ($SiO_2$) or multicomponent glass.

The optical fiber may be a single mode optical fiber (SMF), a multiple mode optical fiber (MMF), a step index-type (SI) optical fiber or a graded index-type (GI) optical fiber.

The means configured to start and stop the photo-induced decomposition of RSNO may supply and intercept light from the external light source to a dark room in which the electrode is disposed.

The photo-induced decomposition may be caused by light having a wavelength range from an ultraviolet region (320 to 350 nm) to a visible region (550 to 590 nm).

An NO selective permeable film may be formed on the electrode.

The RSNO may be at least one selected from the group consisting of S-nitrosoalbumin (Alb-NO), S-nitroso-1-cysteine (CysNO), S-nitroso-1-cysteinemethylester (CMESNO), S-nitroso-d,1-penicillamine (PSNO), S-nitroso-N-acetylcysteineamine (ACSNO), S-nitroso-N-acetyl-1-cysteine (NACysNO), S-nitrosocaptopril (SNOCAP), S-nitroso-mercaptoethylamine, S-nitroso-3-mercapto-propanoic acid, S-nitrosohomocysteine (HcysNO), S-nitroso-b,d-thioglucose, S-nitroso-N-acetyl-d,1-penicillamine (SNAP), S-nitroso-N-acetyl-d,1-penicillaminyl glycine methyl ester and S-nitroso-1-glutathione (GSNO).

Furthermore, the present invention is directed to providing a device for measuring a concentration of RSNO. Here, the device includes a cell configured to mount the amperometric sensor, a pump configured to transport a sample into the cell, and a tubing configured to supply the sample into the cell or discharge the sample from the cell.

The cell may includes passages configured to mount a working electrode, an auxiliary electrode and a reference electrode, respectively, a channel configured to connect the passages and allow the sample to flow in the cell, and a connection unit connected to a tubing configured to supply the sample from the outside into the cell and discharge the sample from the cell to the outside.

The device may include a light source selected from the group consisting of a laser, a halogen lamp, a metal halide lamp, a sodium vapor light, a three-wavelength electrodeless lamp, a LED, an incandescent lamp, a fluorescent lamp and a high-frequency lamp.

BRIEF DESCRIPTION OF THE DRAWINGS

The above and other objects, features and advantages of the present invention will become more apparent to those of ordinary skill in the art by describing in detail exemplary embodiments thereof with reference to the accompanying drawings, in which.

DETAILED DESCRIPTION

The present invention provides an amperometric sensor for measuring a concentration of RSNO, which is able to differentiate an RSNO signal from an NO signal using a single electrode by starting and stopping photo-induced decomposition of RSNO through supply and interception of light into a sample, and measuring an anodic current of NO.

More particularly, the present invention provides an amperometric sensor for measuring a concentration of RSNO, which includes an electrode configured to measure an electric current generated by an oxidation reaction of NO and a means configured to start and stop photo-induced decomposition of RSNO. Here, the electric current is measured by the oxidation reaction of NO before and after the photo-induced decomposition of RSNO.

According to the present invention, one exemplary embodiment of the means configured to start and stop the photo-induced decomposition of RSNO used herein includes a photocatalyst switch configured to introduce the electrode configured to measure an electric current generated by the oxidation reaction of NO into an optical fiber, mount a light source on the optical fiber into which the electrode is introduced, and supply and intercept light from the light source to the optical fiber. That is, the supply and interception of light is controlled by an ON-OFF operation of the photocatalyst switch.

Also, the present invention relates to another exemplary embodiment of a means configured to start and stop the photo-induced decomposition of RSNO. Here, the photo-induced decomposition of RSNO may be started and stopped by setting a space provided with an electrode configured to measure an electric current caused by the oxidation reaction of NO to a dark room environment, and directly supplying and intercepting light from an external light source to a dark room in which the electrode is disposed.

Figure 1:
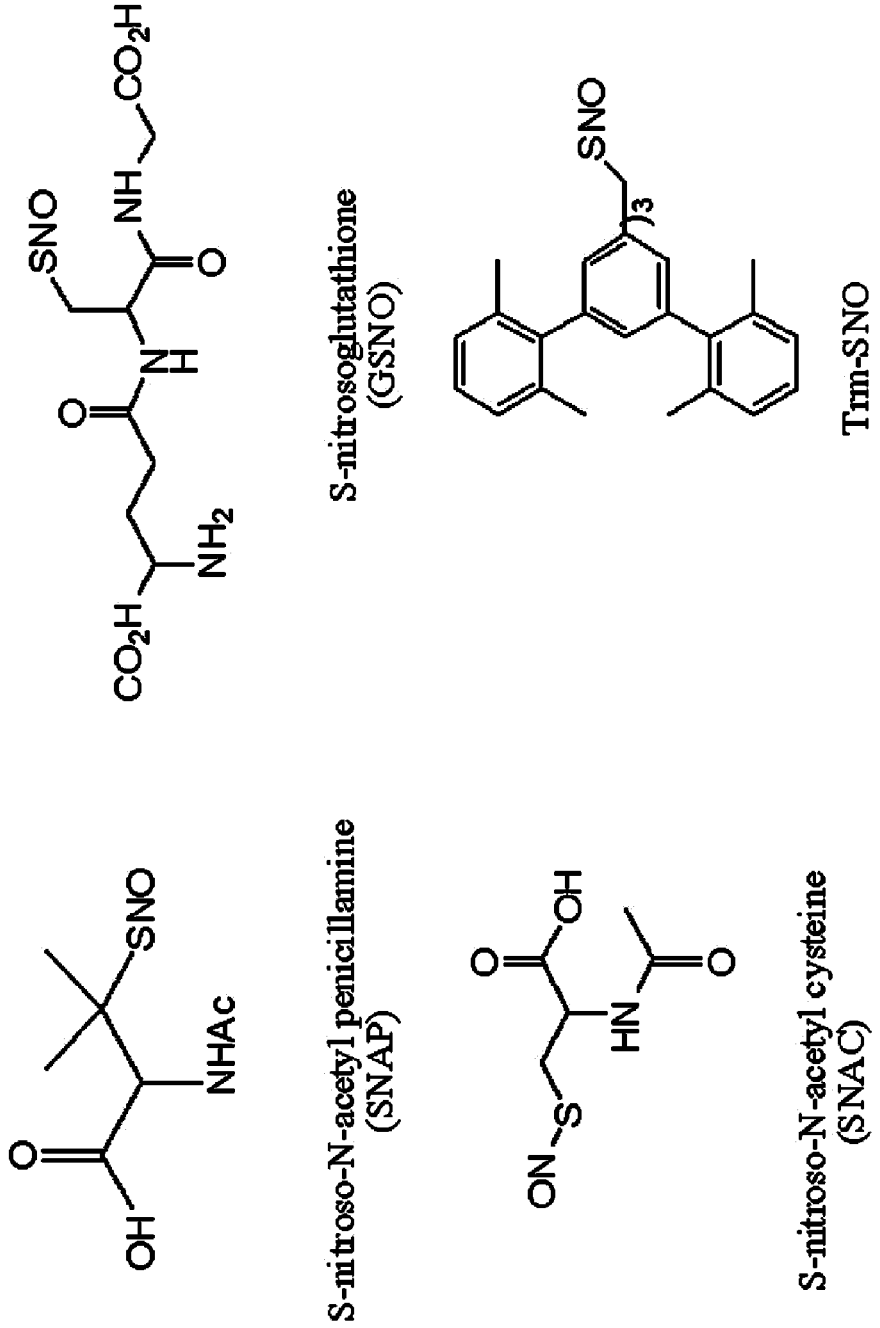
FIG. 1 shows kinds of RSNO compounds present in a living body.
Figure 2:
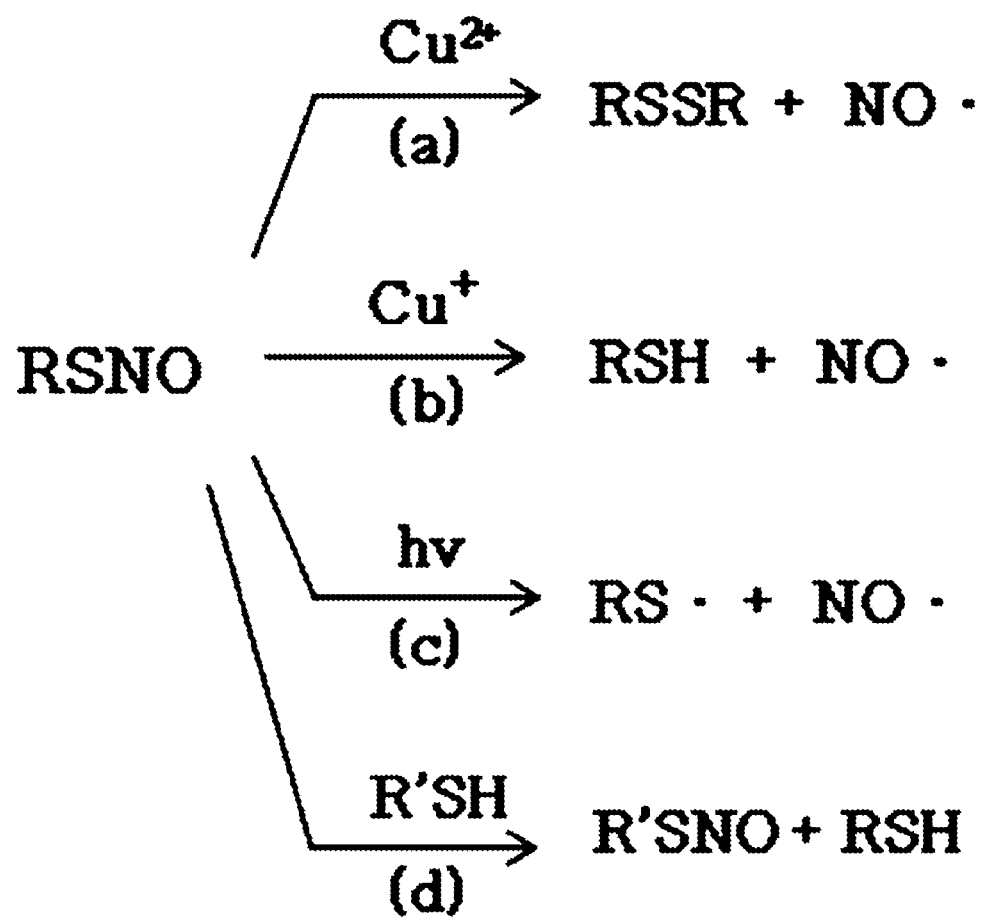
FIG. 2 shows a mechanism of generating NO by decomposition of RSNO.
Figure 3:
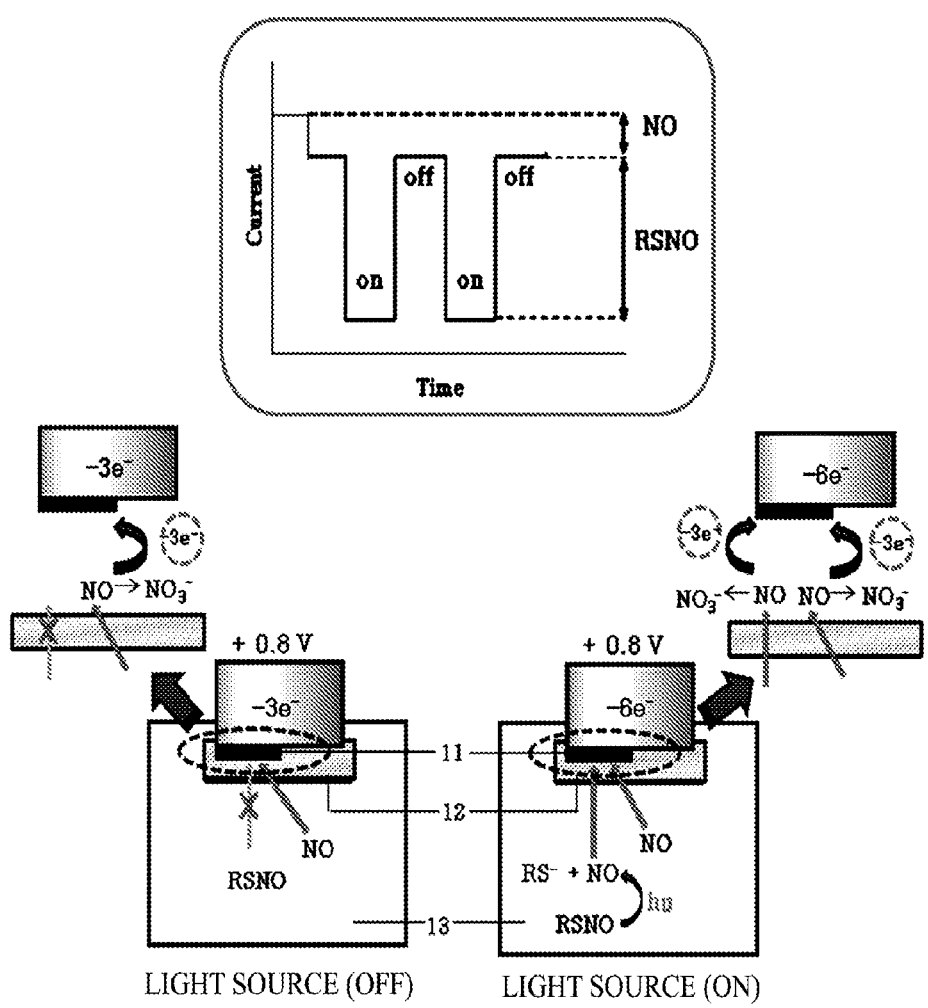
FIG. 3 is a sensitivity curve in an RSNO sensor according to one exemplary embodiment of the present invention.

As shown in FIG. 3, NO is oxidized and loses three electrons for each molecule, and is converted into nitrite ions, forming an anodic current. In this case, the amperometric sensor according to the present invention measures the anodic current. Here, a signal caused by NO originally present in a sample is obtained in an OFF state of the light source, and a signal of NO generated by the photo-induced decomposition of RSNO appears in an ON state of the light source in addition to the signal of NO. Therefore, the amperometric sensor according to the present invention may obtain separate signals generated from NO and RSNO.

According to the present invention, when the photo-induced decomposition of RSNO is started and stopped using the photocatalyst switch, an optical fiber used as a means configured to deliver light from a light source has a structure in which a core made of a material having a high refractive index is uniformly surrounded by a cladding made of a material having a low refractive index, and may deliver light at a very high speed without loss using the total reflection in the core and the cladding.

In the present invention, the core has a diameter of 250 μm to 3 mm, and is made of plastic, silica ($SiO_2$) or multicomponent glass. Therefore, the optical fiber has good heat resistance and a wavelength region from an ultraviolet region to a visible region as a wavelength transmission region of light, and may include a single mode optical fiber (SMF), a multiple mode optical fiber (MMF), a step index-type (SI) optical fiber, or a graded index-type (GI) optical fiber.

In the present invention, when the optical fiber and the photocatalyst switch are used as the means configured to start and stop the photo-induced decomposition of RSNO, an electrode configured to measure an anodic current of NO may be used in a state where the electrode is introduced into the optical fiber. That is, the optical fiber is used as a body into which the electrode is introduced. A method of introducing an electrode into an optical fiber may include a method of coating a metallic or non-metallic conductive material using a screen printing method or the like, a method of forming a metal thin film using a metal deposition method (i.e., sputtering), or a method using a metal wire, rod or plate.

In order to form an electrode using the screen printing method or the like, a mixed composition, which includes a paraffinic oil and at least one metallic or non-metallic conductive material selected from the group consisting of gold, carbon, silver, platinum and a mixture of silver and carbon, may be coated on the optical fiber as an electrode material. In this case, a region in which the electrode material is coated on the optical fiber may be an end surface, a lateral surface, or some or all of the end surface and lateral surface of the cylindrical optical fiber. After the coating, the introduction of the electrode is completed by drying the electrode material. Preferably, the introduced electrode is connected to an operating circuit of the amperometric sensor by means of a conducting wire, and the optical fiber including the electrode is used in a state where a surface of the optical fiber is tubed with an insulating material.

In order to form an electrode on an optical fiber using the metal deposition method, a metal plate prepared by combining at least one or two conductive metals selected from the group consisting of platinum, gold, silver, vanadium, niobium, tantalum, indium, titanium, nickel, molybdenum, iron, copper, cobalt, chromium, bismuth, aluminum, and nickel chromium may be targeted to deposit a metal thin film on the optical fiber. In this case, a region in which the metal thin film is deposited on the optical fiber may be an end surface, a lateral surface, or both the end surface and lateral surface of the cylindrical optical fiber. Also, the introduced electrode in a metal thin film form may be connected to an operating circuit of the amperometric sensor by means of a conducting wire, and the optical fiber including the electrode may be used in a state in which a surface of the optical fiber is tubed with an insulating material.

Using a conductive wire, rod or plate as an electrode into which an optical fiber is introduced means that a wire, rod or plate formed of a material obtained by combining at least one or two conductive materials selected from the group consisting of platinum, gold, silver, vanadium, silicon oxide, niobium, tantalum, indium, titanium, nickel, molybdenum, iron, copper, cobalt, chromium, graphite, bismuth, aluminum, zinc oxide manganese and nickel chromium, is attached to an optical fiber by means of an insulating adhesive, and used. In this case, a region of the optical fiber to which the electrode in a wire, rod or plate shape is attached may be an end surface, a lateral surface, or both the end surface and lateral surface of the cylindrical optical fiber. Also, the introduced electrode may be connected to an operating circuit of the amperometric sensor by means of a conducting wire, and the optical fiber including the electrode may be used in a state where a surface of the optical fiber is tubed with an insulating material.

Since light is easily transmitted and a surface coated with an electrode is made flat when an electrode material is coated using the screen printing method or the like to introduce the electrode into an optical fiber, a surface of the optical fiber to be coated with the electrode material may be rubbed even with sandpaper or the like. Thereafter, a mixed composition including carbon is coated as an electrode material on a surface of the optical fiber, and dried to form an electrode. Here, a surface of the electrode may be further plated with platinum so as to enlarge the surface of the electrode and enhance electrochemical activities.

Meanwhile, in the present invention, as the means configured to start and stop the photo-induced decomposition of RSNO, electrodes used when an electrode is disposed in a dark room environment and light is supplied from an external light source to a dark room in which the electrode is disposed may be used without limitation as long as they are in a generally used shape such as a disk electrode, a coin electrode, a rod electrode or the like.

Also, the amperometric sensor according to the present invention includes a film configured to selectively transmit NO through a surface of an electrode so as to prevent an inhibition action caused by nuisance species in measurement of an anodic current of NO. The film may be formed by immersing an electrode in a sol-gel solution of a film-forming material and coating the film-forming material on a surface of the electrode.

In the present invention, as one exemplary embodiment of a film-forming process, a film may be formed through a self-assembly reaction in a sol-gel process by mixing a silane monomer, methyltrimethoxysilane (MTMOS) having a purity of 98% or more, used to form a backbone with a perflourinated silane monomer, (heptadecafluoro-1,1,2,2-tetrahydrodecyl)trimethoxysilane (17FTMS), used to give a film lipophilicity.

The self-assembly reaction is performed through a route represented by the following Scheme 1.

species having hydrophilicity such as nitrite ions, ascorbic acid, uric acid or acetaminophen may be blocked by preventing the nuisance species from passing through the lipophilic membrane (Shin, J. H. et al., Anal. Chem. 2008, 80, 6850-6859).

The electrode used in the amperometric sensor according to the present invention as described above is configured to measure an electric current, that is, an anodic current, generated by an oxidation reaction of NO. Preferably, in the present invention, a three-electrode system using the electrode as a working electrode and also using a reference electrode and an auxiliary electrode is provided. In the present invention, an anodic current of NO is also measured using chronoamperometry.

According to the present invention, a device for measuring a concentration of RSNO is provided. Here, the device is preferably configured to form the same environment as measured in a blood vessel in a human body by introducing the amperometric sensor into a flow injection analysis (FIA) system and measuring electrochemical signals of RSNO and NO in a flowing sample.

The device for measuring a concentration of RSNO includes a cell configured to mount a sensor and a pump and a tubing configured to deliver a sample into the cell. Also, the cell is configured to include passages configured to mount a working electrode, an auxiliary electrode and a reference electrode, respectively, which are included in the amperometric sensor according to the present invention, a channel configured to connect the passages and serve a movement space of the sample into the cell, and a connection unit connected to a tubing configured to supply the sample from the outside into the cell and discharge the sample from the cell to the outside.

In the device, a laser, a halogen lamp, a metal halide lamp, a sodium vapor light, a three-wavelength electrodeless lamp, an LED, an incandescent lamp, a fluorescent lamp or a high-frequency lamp may also be used as the light source configured to supply light to the sample. When an optical fiber and a photocatalyst switch are used as means for photo-induced decomposition of RSNO, such a light source

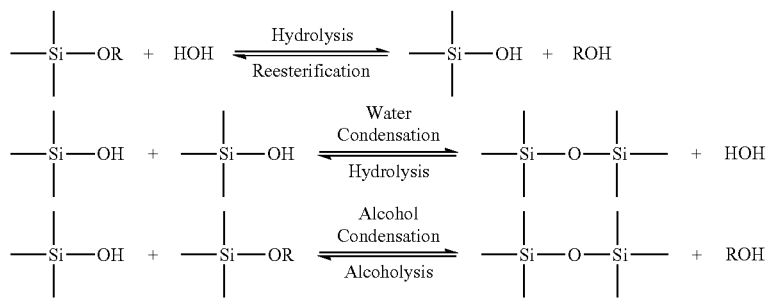

Scheme 1

The term "17" in the 17FTMS refers to the number of fluorine groups included in a silane monomer. Since a fluorine group serves to reduce a surface energy, which is one of chemical characteristics for surface modifications, the more fluorine groups there are the higher a film formed therefrom shows lipophilicity. NO is a lipophilic material that is delivered through a lipophilic lipid membrane even in a living body. Therefore, in the present invention, a surface of the electrode is provided with a lipophilic membrane to selectively transmit NO. Meanwhile, an action of nuisance is controlled by an ON-OFF operation of the photocatalyst switch, and is used as the light source configured to supply and intercept light into the optical fiber. When an electrode is disposed in a dark room, and light is directly supplied from a light source to the dark room, the light source may be used as an external light source configured to supply light to the dark room.

Kinds of RSNO which may be measured using the amperometric sensor of the present invention include S-nitrosoalbumin (Alb-NO), S-nitroso-1-cysteine (CysNO), S-nitroso-1-cysteinemethylester (CMESNO), S-nitroso-d,1-penicillamine (PSNO), S-nitroso-N-acetylcysteineamine (ACSNO), S-nitroso-N-acetyl-1-cysteine (NACysNO), S-nitrosocaptopril (SNOCAP), S-nitroso-mercaptoethylamine, S-nitroso-3-mercapto-propanoic acid, S-nitrosohomocysteine (HcysNO), S-nitroso-b,d-thioglucose, S-nitroso-N-acetyl-d,1-penicillamine (SNAP), S-nitroso-N-acetyl-d,1-penicillaminyl glycine methyl ester and S-nitroso-1-glutathione (GSNO), which may be present in human bodies or be artificially synthesized.

Hereinafter, the present invention will be described in detail with reference to Examples thereof. However, it should be understood that the Examples are provided to help better understanding of the present invention, and the present invention is not limited thereto.

EXAMPLE 1

Figure 4:
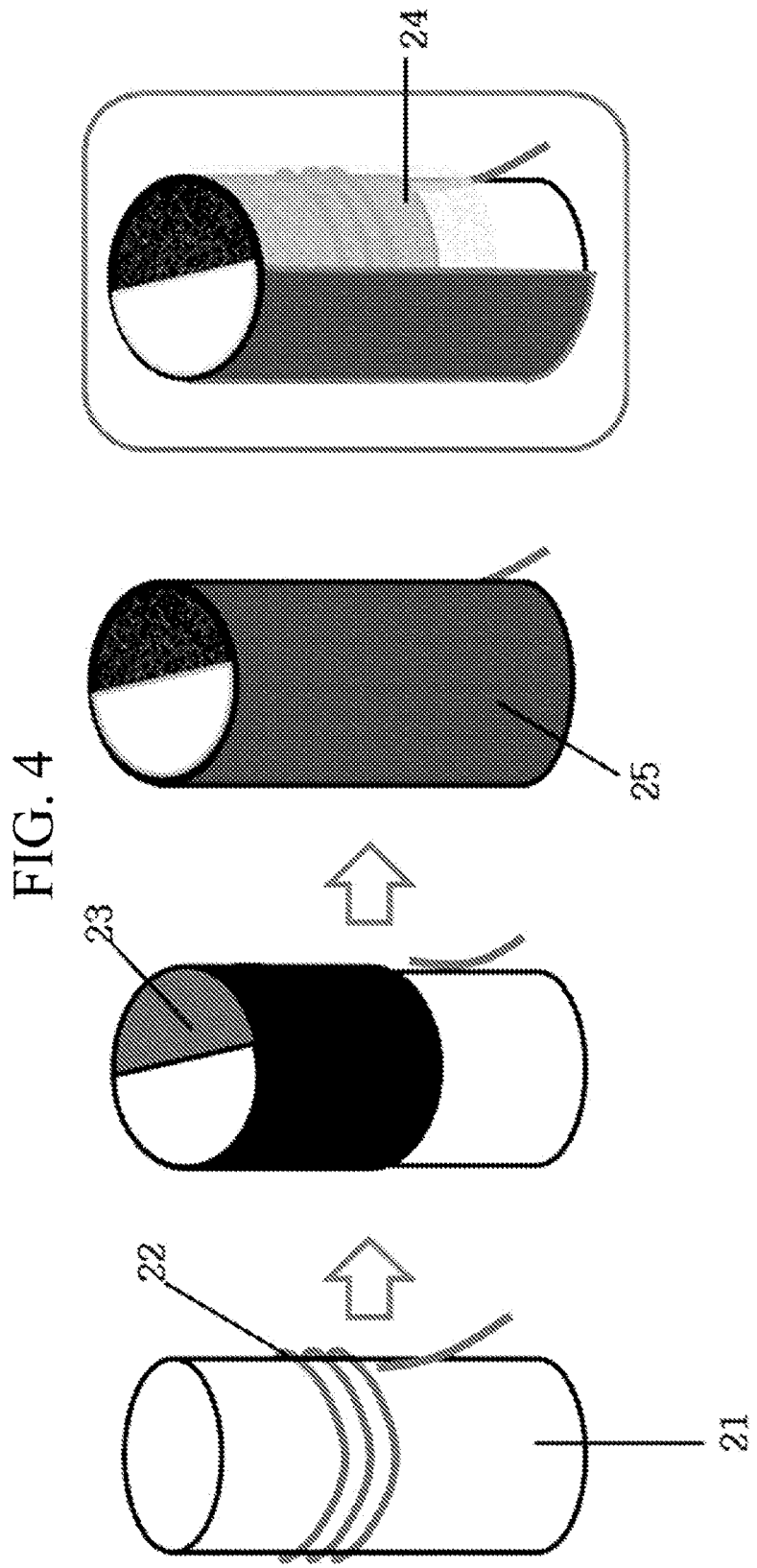
FIG. 4 is an exploded perspective view showing a process flow diagram of an electrode introduced into an optical fiber, and an electrode manufactured according to one exemplary embodiment of the present invention.

Manufacture of Amperometric Sensor for Measuring Concentration of RSNO (1) Manufacture of Electrode for RSNO Sensor Using Optical Fiber FIG. 4 shows a process of manufacturing an electrode introduced into an optical fiber as a component of an RSNO sensor, and a structure of an electrode manufactured according to one exemplary embodiment of the present invention.

An optical fiber 21 used as a body of the electrode was selected and made of a general resin such as polymethylmethacrylate (PMMA). An optical fiber was cut into pieces having lengths of 10 cm, and both end surfaces of the optical fiber were rubbed with sandpaper in a sequence from rough to fine (100, 400, 2000 and 4000 grits). Then, a lateral surface of the optical fiber was wound with a commercialized alloy conducting wire containing lead to install an operating circuit connection line 22. Thereafter, approximately a half of the end surface of the optical fiber was coated with a carbon paste (DUPONT, Lot #RKP306) to form a working electrode 23, and the operating circuit connection line 22 and a lateral surface of the optical fiber were than coated with a carbon paste to electrically connect the working electrode 23 with the connection line 22. Then, the carbon paste coated on the optical fiber was dried for 10 minutes using a dryer. When the drying was completed, an epoxy resin was applied to a carbon-coated region rather than the electrode to form an insulating film 24, the epoxy resin was dried, and a constriction tube was then used to form a coating 25 of the electrode.

In addition, in order to form a Pt black layer on a surface of the working electrode 23, the working electrode 23 was subjected to cyclic voltammetry (CV). Here, the CV was performed eight times in a mixed solution including 3% by weight of chloroplatinic acid ($H_2PtCl_6$), 0.029% by weight of lead acetate and 97% by weight of water at a scanning rate of 50 mV/s over an electric potential region of –0.1 V to 0.5 V (vs. Ag/AgCl).

(2) Formation of NO Selective Permeable Film

In order to manufacture an NO selective permeable film, 311.25 μl of ethanol was added as a solvent into a brown microcentrifuge tube for intercepting light, and 51 μl of MTMOS having a purity of 98% or more was added as a silane monomer used to form a backbone, and the resulting solution was mixed. Then, 12.75 μl of 17FTMS was added as a silane monomer used to supply a fluorine (F) group, and then vortexed to mix the solution. 80 μl of distilled water and 5 μl of 0.5 M hydrochloric acid were added as an acid catalyst for hydrolysis. The resulting mixture was vigorously stirred for 2 hours with a magnetic bar to sufficiently progress the reaction.

The manufactured electrode was immersed in the prepared sol-gel solution (xerogel) to form an NO selective permeable film on a surface of the electrode, and then dried at room temperature for 24 hours.

Evaluation of Sensitivity to NO and Nuisance Species 8 ml of a buffer (pH 7.4 PBS 0.1M (NaCl 50 mM)) was put into a 10-ml falcon tube, and then bubbled with nitrogen gas for 30 minutes. Thereafter, the falcon tube containing the solution bubbled with the nitrogen gas was dipped into iced water to facilitate fusing of NO, and NO was then fused for 20 minutes to prepare a blue NO saturated solution having a concentration of 1.9 mM. NO solutions having various NO concentrations were prepared from the saturated solution. Also, nitrite ion, ascorbic acid, uric acid and acetaminophen solutions having concentrations of 50 μM were prepared as nuisance species.

Figure 5:
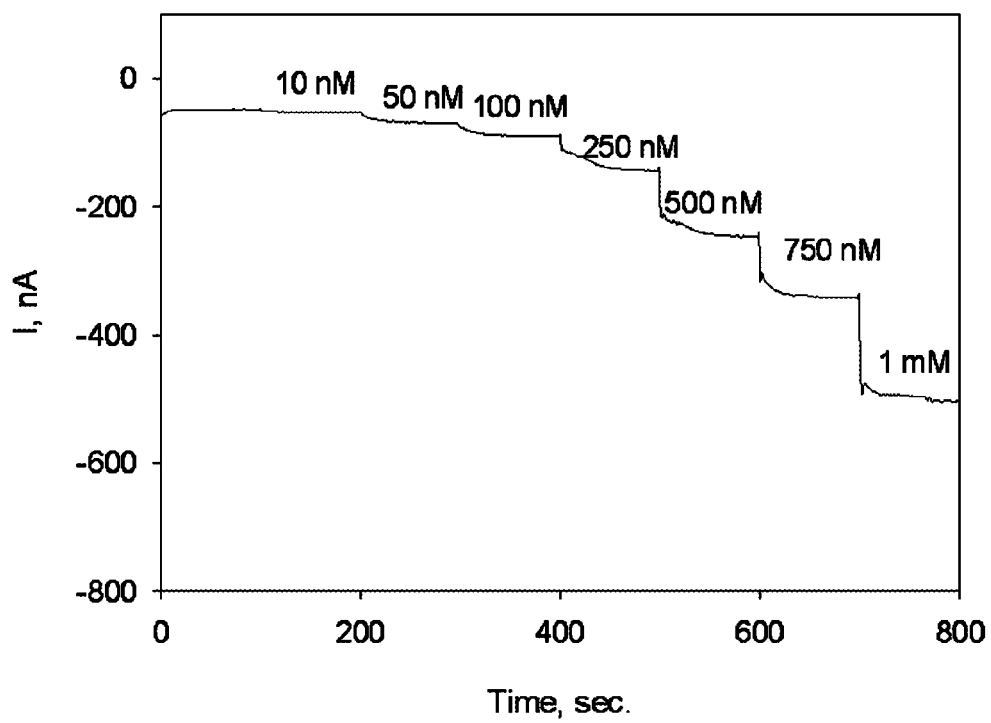
FIG. 5 is a sensitivity curve of NO in the RSNO sensor according to one exemplary embodiment of the present invention.
Figure 6:
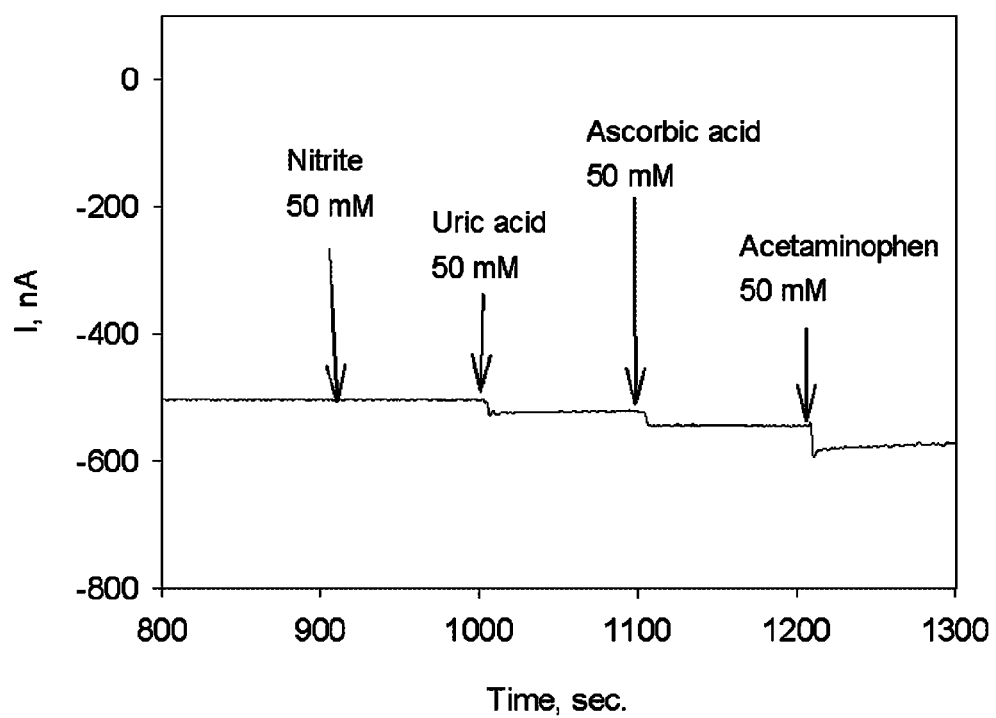
FIG. 6 is a sensitivity curve of nitrite ions, ascorbic acid, uric acid and acetaminophen in the RSNO sensor according to one exemplary embodiment of the present invention.

The manufactured electrodes were measured for anodic current from each of the prepared solutions using an electrochemical measurement device, Electrochemical Analyzer Workstation 760D (CH Instrument). An applied electric potential was 700 mV (vs. Ag/AgCl). The measurement results on the NO solutions were represented in a sensitivity curve as shown in FIG. 5, and the measurement results on the nuisance species solutions were represented in a sensitivity curve as shown in FIG. 6.

An anodic current was increased with an increasing concentration of NO. Meanwhile, the nuisance species showed very low sensitivity even at a concentration of 50 μM, which is 50 times the maximum NO concentration of 1 μM.

Therefore, it was seen that the electrode manufactured according to the present invention was selective to NO, and its sensitivity was varied according to a concentration of NO.

EXAMPLE 2

Figure 7:
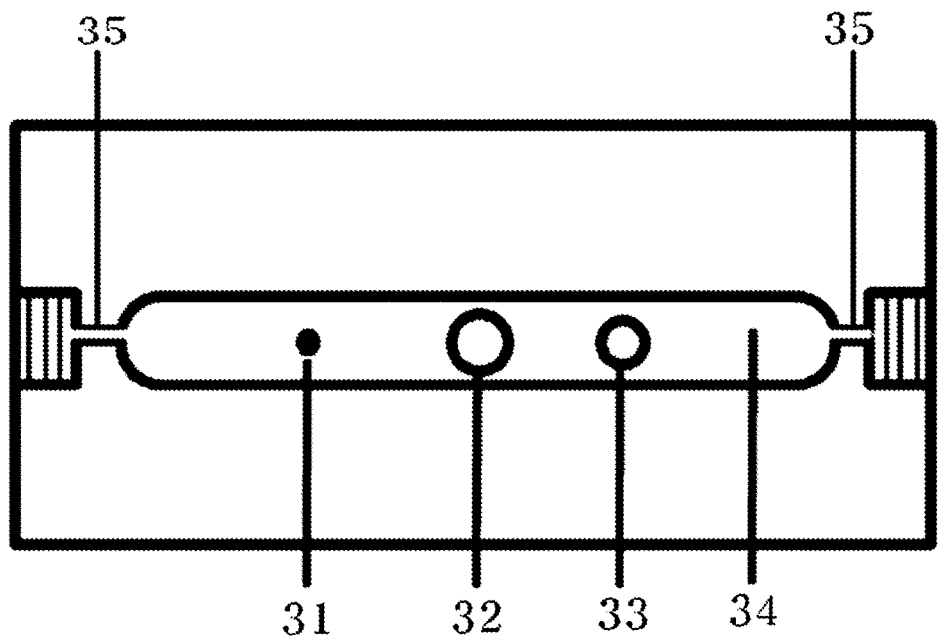
FIGS. 7 and 8 are a cross-sectional view and a plane view showing a cell in which a sensor according to one exemplary embodiment of the present invention is mounted.
Figure 8:
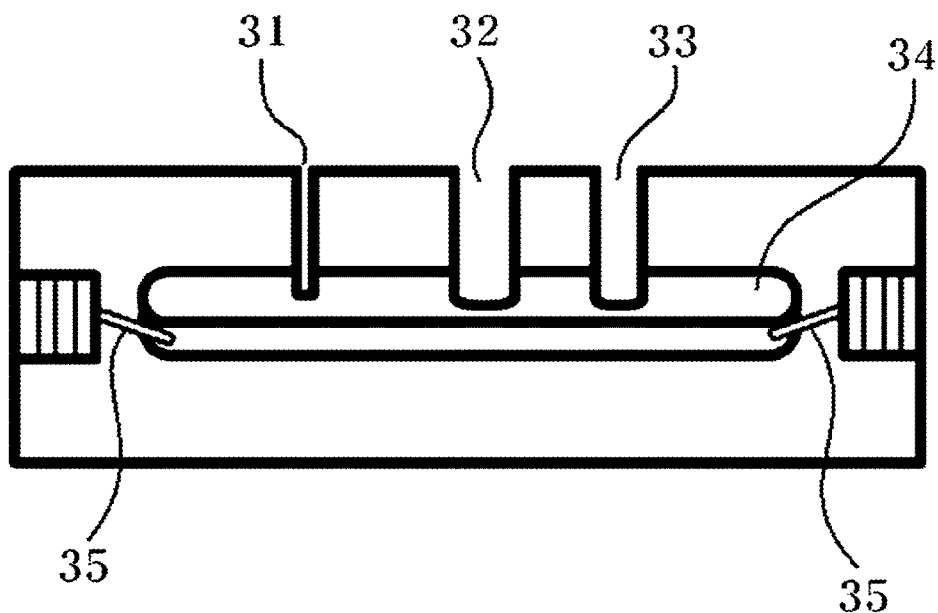

Manufacture of Device for Simultaneously Measuring Concentrations of RSNO and RSNO/NO (1) Manufacture of cell used in device for simultaneously measuring concentrations of RSNO and RSNO/NO FIGS. 7 and 8 show shapes of cells used in a device for measuring a concentration of RSNO using an amperometric sensor of the present invention. A cell was made of an acrylic resin, and manufactured in a rectangular shape. As shown in FIG. 7, the cell had a longitudinal length of 6.7 cm and a vertical length of 3.8 cm, when viewed from the top, and the cell had a height of 2.6 cm, when seen from the side as shown in FIG. 8.

Passages were formed to mount a working electrode, a reference electrode and an auxiliary electrode from a top surface of the cell. That is, a passage 31 into which an auxiliary electrode having a diameter of 0.5 mm would be inserted was formed at a position spaced 2.3 cm apart from a left end of the cell, a passage 32 into which a reference electrode having a diameter of 0.45 cm would be inserted was formed at a distance of 0.8 cm from the position of the passage 31, and a passage 33 into which a working electrode having a diameter of 0.35 cm would be inserted was formed at a distance of 0.5 cm from the position of the passage 32. Also, the channel 34 was disposed below the passages at a distance of 1.4 cm from a top surface of the cell, and arranged in a vertical direction with respect to the passages, forming a channel connecting the three passages. The channel had a width of 0.5 cm and a height of 0.1 cm. An O-ring was mounted on each passage of the electrode to prevent leakage of a sample. In addition, the connection unit 35 connected to a tubing configured to supply a sample from the outside into the cell and then discharge the sample from the cell to the outside was formed at a distance of 1.4 cm from the top surface of the cell. The sample supplied from the outside by the tubing and the connection unit 35 flowed through the channel, and was discharged by the connection unit 35 and the tubing.

(2) Configuration of FIA System

Figure 9:
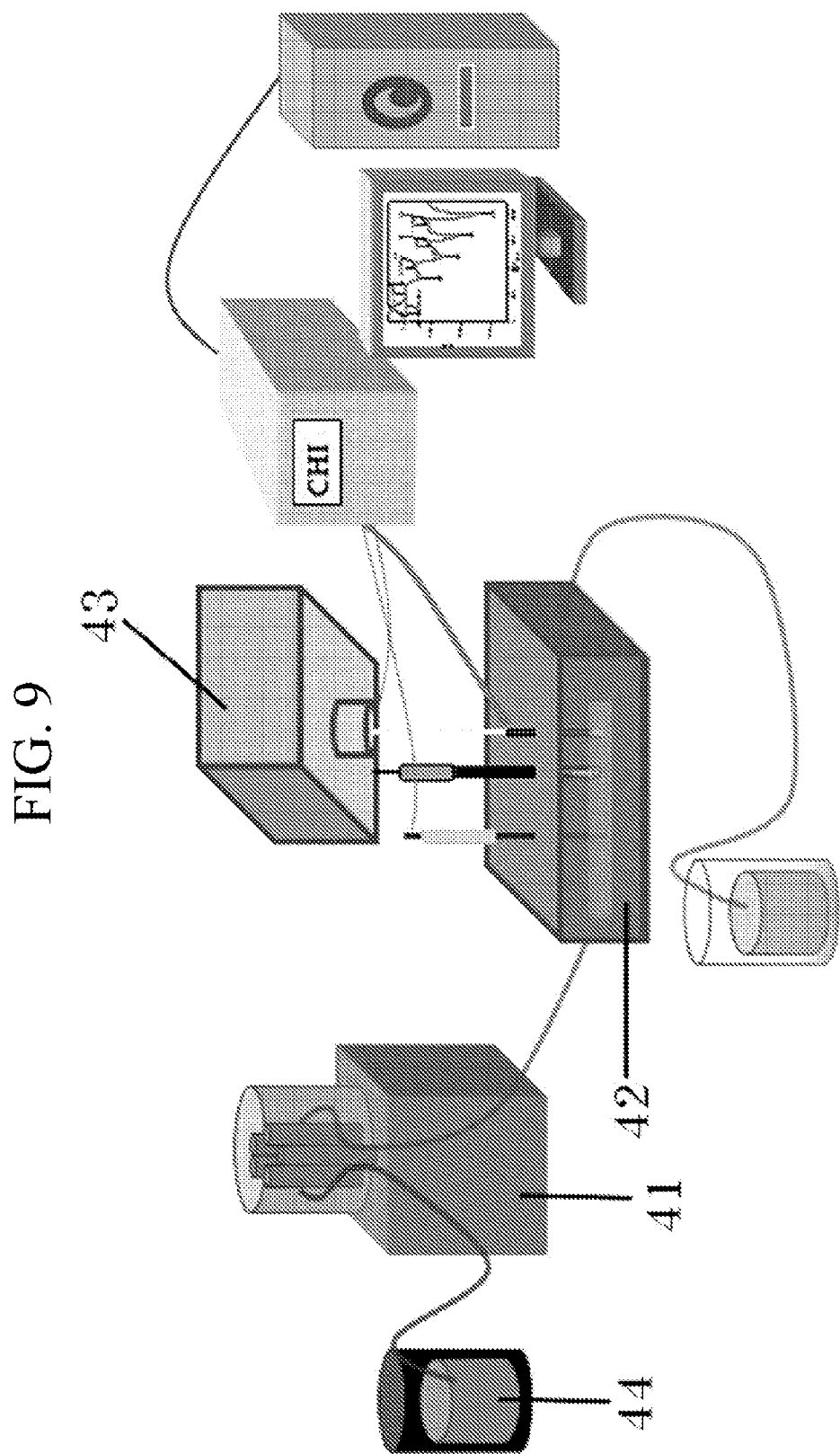
FIG. 9 is a schematic view of a device for measuring a concentration of RSNO according to one exemplary embodiment of the present invention.

The electrode manufactured in Example 1 was mounted as a working electrode onto the manufactured cell, and a reference electrode and an auxiliary electrode were also mounted onto the cell. As shown in FIG. 9, a device for measuring a concentration of RSNO was manufactured, including a pump 41 configure to force a sample 44 to flow in a cell and a light source 43 configured to supply light to the cell in addition to a cell 42.

Evaluation of Sensitivity to Clinical Concentration of SNAP

A signal was measured in a clinical concentration range of RNSO using the manufactured device, depending on the concentration of RNSO.

A 0.1 M phosphate buffer (140 mM KCl, 16 $\mu$M ethylenediaminetetraacetic acid, pH 7.4) was used as a blank solution, and an applied electric potential was 700 mV (vs. Ag/AgCl). The signal was measured using SNAP as RNSO. SNAP solutions were prepared at different concentrations of 1, 2, 5 and 10 $\mu$M. 30 ml of the solution was added into 40-ml vials, and the vials were wrapped with silver paper to intercept light, so that SNAP could not be decomposed by the light. The blank solution or the sample solution was delivered to a cell using a peristaltic pump having an operating principle of peristalsis, and a transport rate was set to a fixed value of 10 revolutions per minute (rpm).

The electrode was stabilized in the blank solution for 4 hours. The stabilized electrode had an electric current of approximately 40 nA. Then, a sufficient amount of a 2 $\mu$M SNAP solution flowed to be smoothly circulated all over the device. A stabilizing signal of the SNAP solution was collected for 100 seconds in an OFF state of the photocatalyst switch, and the photocatalyst switch was then turned on. An anodic current of NO generated from RSNO by light transmitted through the optical fiber was measured for 300 seconds. After 300 seconds of the measurement, the photocatalyst switch was turned off again, and a stabilizing signal was then collected for 100 seconds. Thereafter, the collection of the stabilizing signal was temporarily stopped, and the electrode was washed for 10 minutes by allowing a blank solution to flow in the electrode.

Figure 10:
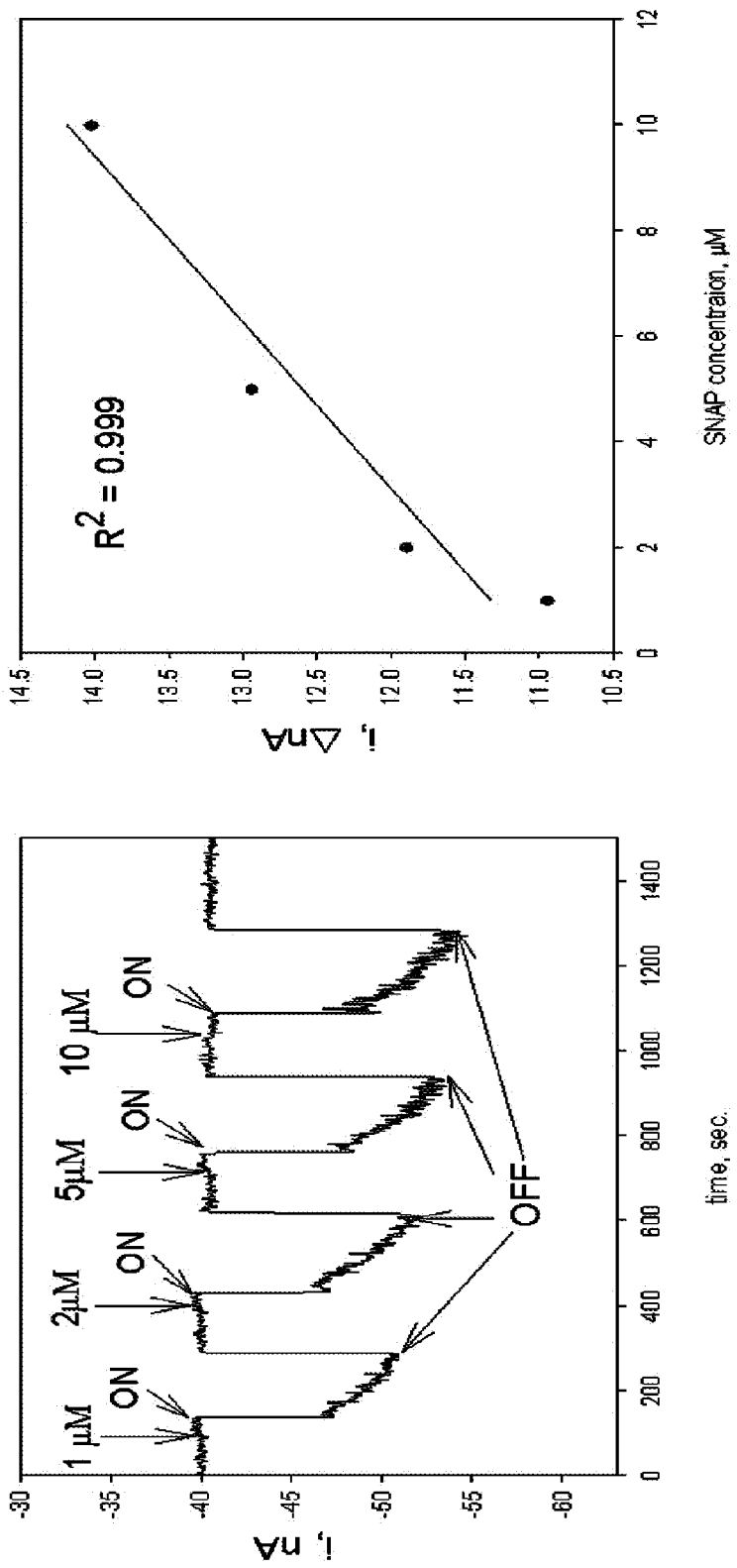
FIG. 10 is a sensitivity curve and an assay curve of SNAP when present in a clinical concentration in the RSNO sensor according to one exemplary embodiment of the present invention.

Various signals for the SNAP solution were measured by repeating the above-mentioned procedures. The measurement results are shown in FIG. 10. It was confirmed that the signals were increased in a concentration-dependent manner. Also, an assay curve obtained from the electric current values at the different concentrations showed linearity of 0.998. From these facts, it was seen that the device according to the present invention showed good sensitivity to SNAP having a concentration of 1 to 10 $\mu$M.

Evaluation of Sensitivity to Low Concentration Range of SNAP

Figure 11:
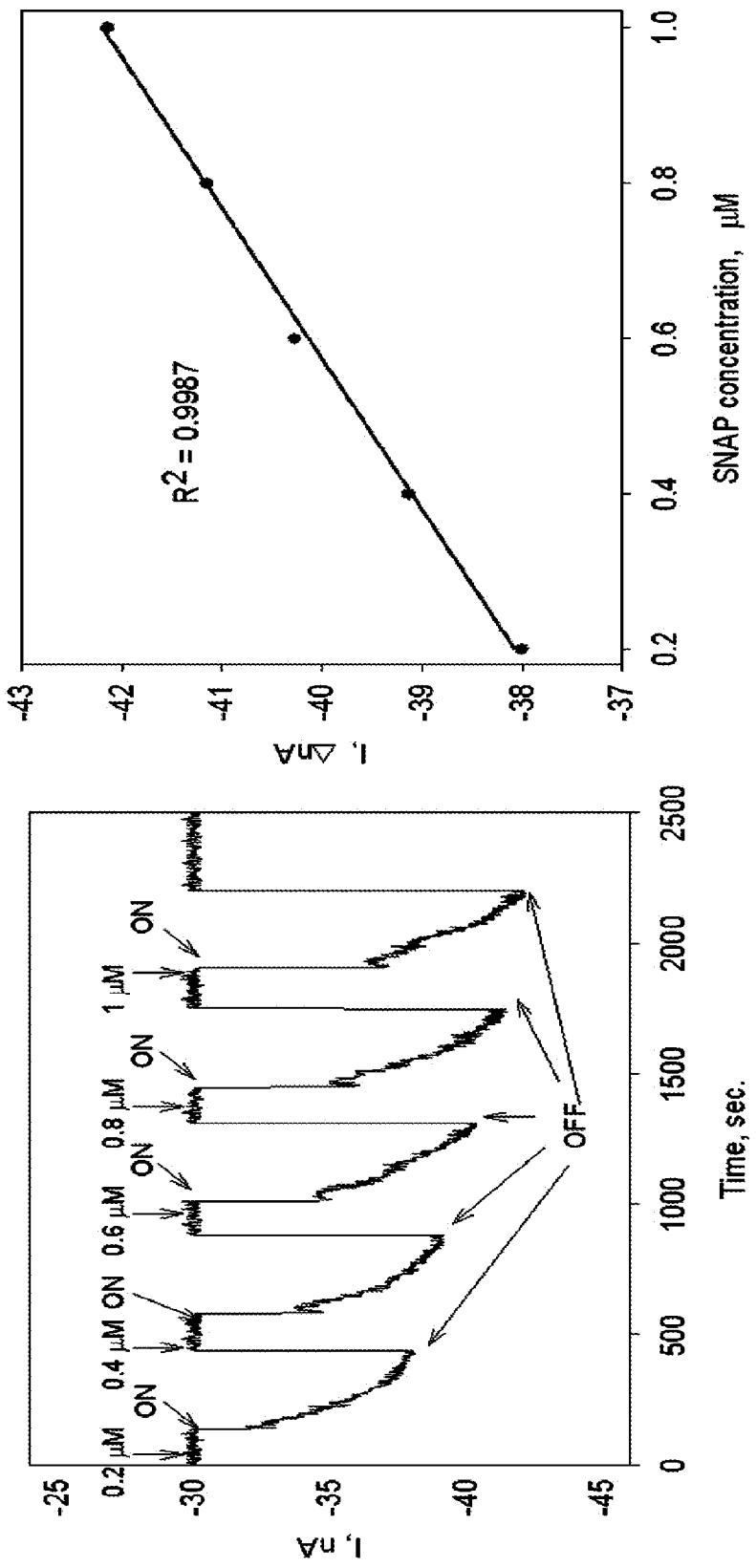
FIG. 11 is a sensitivity curve and an assay curve of SNAP when present in a low concentration in the RSNO sensor according to one exemplary embodiment of the present invention.

SNAP solutions were prepared at different concentrations of 0.2, 0.4, 0.6, 0.8 and 1 $\mu$M. A signal for each solution was measured in the same manner as described above. The measurement results are shown in FIG. 11. It was confirmed that the signals were increased even in a low concentration range of the SNAP solution in a concentration-dependent manner. Also, an assay curve obtained from the electric current values at the different concentrations showed very good linearity of 0.999. From these facts, it was seen that the device according to the present invention showed good sensitivity to SNAP having a concentration range of 0.2 to 1 $\mu$M.

Evaluation of Sensitivity to High Concentration Range of SNAP

Figure 12:
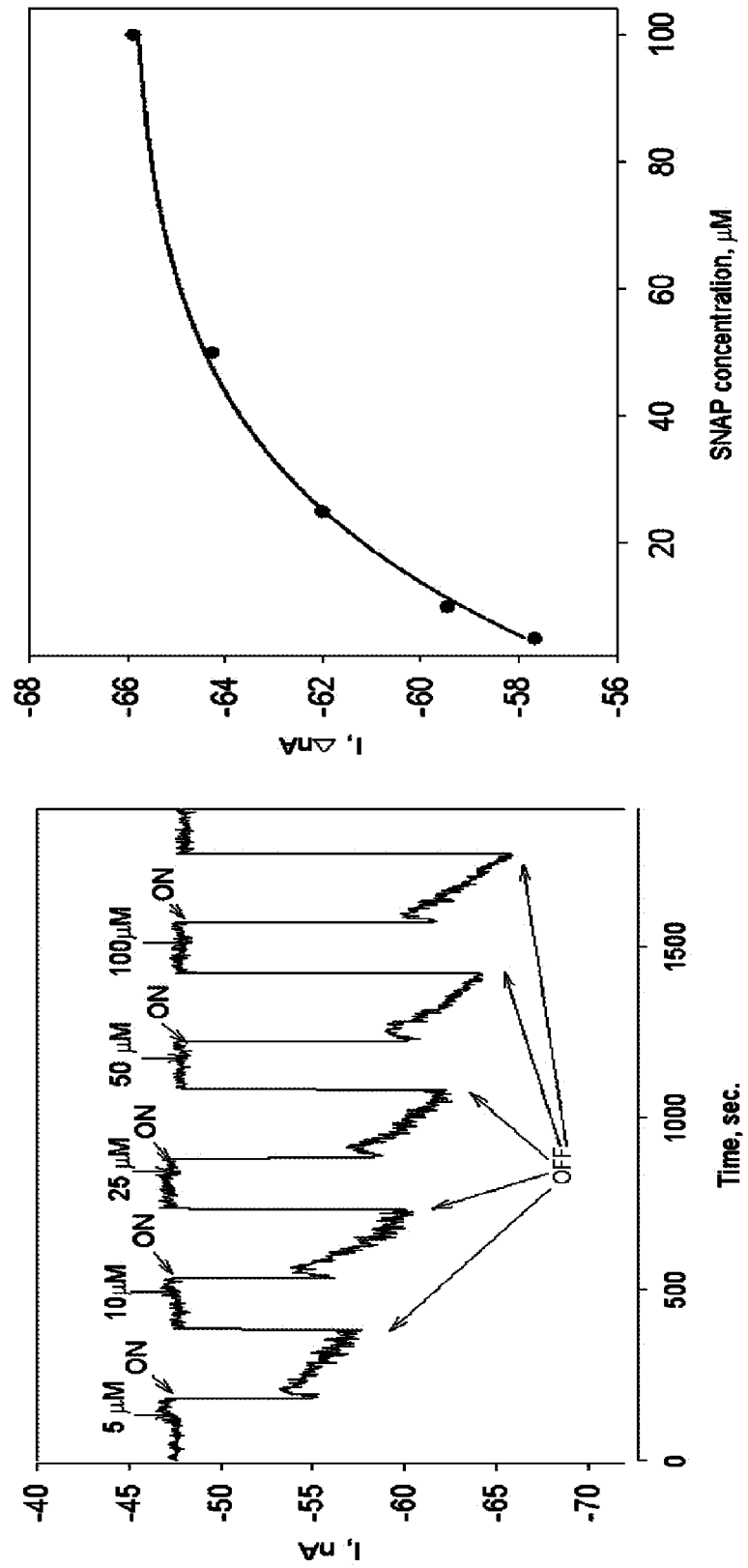
FIG. 12 is a sensitivity curve and an assay curve of SNAP when present in a high concentration in the RSNO sensor according to one exemplary embodiment of the present invention.

SNAP solutions were prepared at different concentrations of 5, 10, 25, 50 and 100 $\mu$M. A signal for each solution was measured in the same manner as described above. The measurement results are shown in FIG. 12. It was confirmed that the signals were increased even in a high concentration range of the SNAP solution in a concentration-dependent manner. Also, an assay curve obtained from the electric current values at the different concentrations showed a detection limit at a concentration of 50 $\mu$M or more. However, it was seen that the device according to the present invention showed good sensitivity to SNAP having a concentration range of 5 to 50 $\mu$M.

Measurement of Concentrations of NO and RSNO

Figure 13:
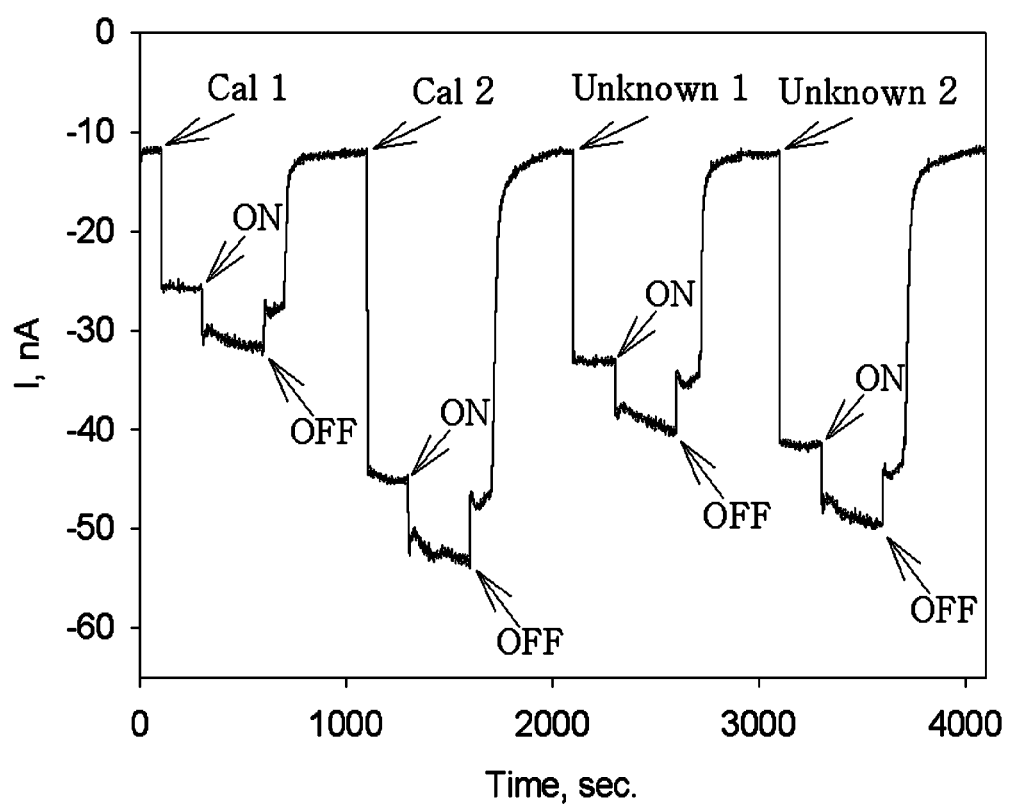
FIGS. 13 to 15 are a sensitivity curve of SNAP and assay curves of RSNO and NO in the RSNO sensor according to one exemplary embodiment of the present invention.

A Cal solution 1 (2 nM NO, 0.2 $\mu$M SNAP), a Cal solution 2 (10 nM NO, 1 $\mu$M SNAP) and unknown sample solutions 1 and 2 whose NO and SNAP concentrations were within the concentration ranges of the Cal solutions 1 and 2 were prepared. A signal for each solution was measured in the same manner as described above. The measurement results are shown in FIG. 13. A signal measured after injection of a sample was generated by NO, and a signal measured when a photocatalyst switch was turned on was generated by RSNO.

Figure 14:
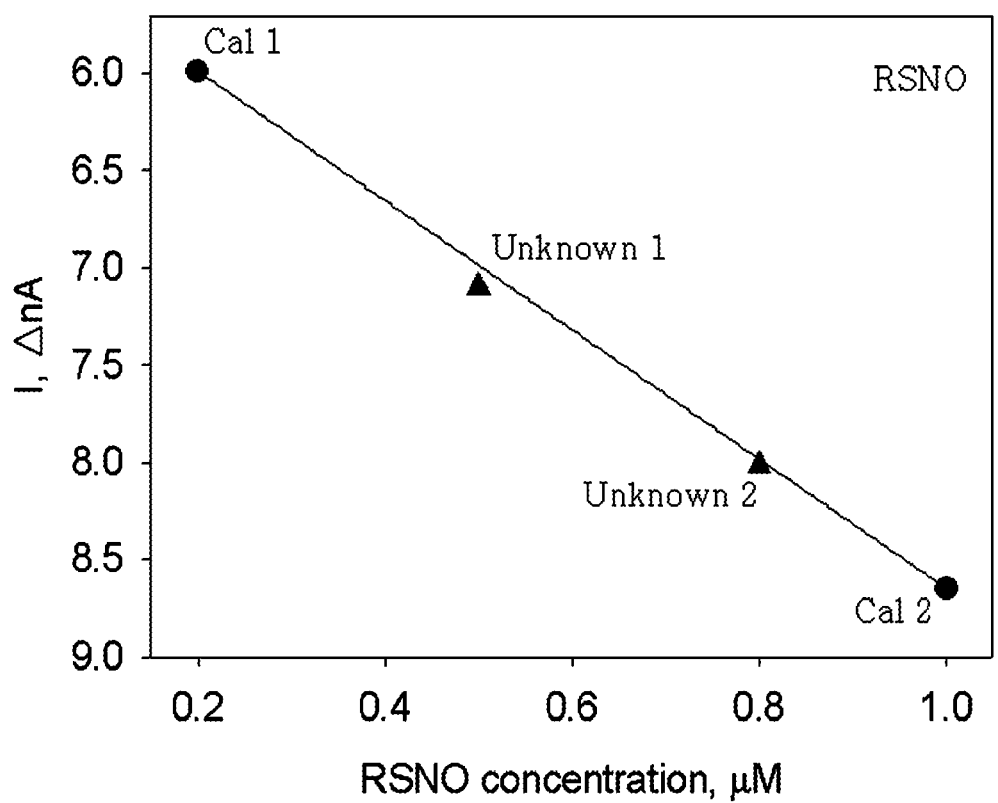
Figure 15:
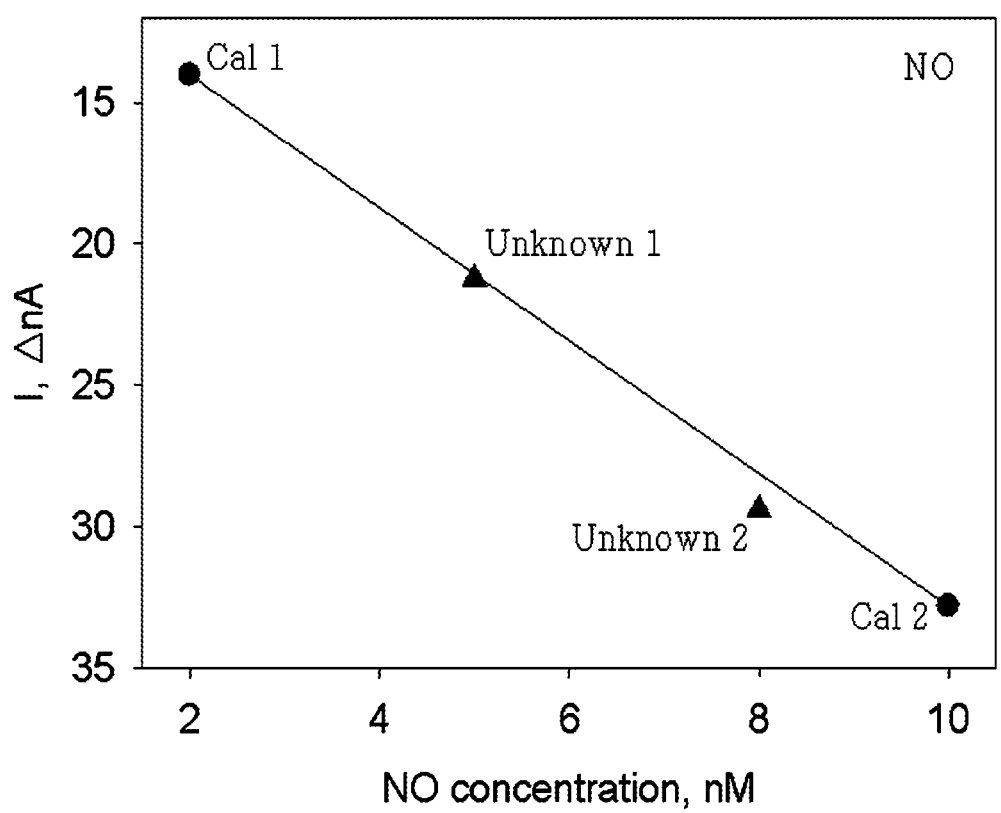

As shown in FIGS. 14 and 15, respective assay curves of NO and SNAP for the Cal solution 1 (0.2 $\mu$M RSNO, 2 nM NO) and the Cal solution 2 (1 $\mu$M RSNO, 10 nM NO) were obtained, and electric current values obtained from the unknown sample solutions 1 and 2 were marked on the assay curves. As a result, it was revealed that the concentrations of NO and RSNO obtained from the unknown sample solutions were included in both of the assay curves of NO and RSNO, and the two materials could be differentiated from each other. Meanwhile, it was seen from FIG. 13 that the electrode was readily recovered into a stabilized state prior to flow of the sample when a blank solution re-flowed to wash the electrode The device of the present invention may measure separate signals from RSNO and NO using a single electrode when a concentration of RSNO is measured. Therefore, it is possible to reliably measure RSNO by excluding an inhibition action caused by NO.

Also, the amperometric sensor according to the present invention is simple in structure and easy to manufacture and may be applied to manufacture of a small electrode. Therefore, the present invention may be used to develop a means capable of directly measuring a concentration of RSNO in a living body.

The present invention has been shown and described with reference to certain exemplary embodiments thereof, it will be understood by those skilled in the art that various changes in form and details may be made therein without departing from the scope of the invention as defined by the appended claims.

What is claimed is:

1. An apparatus, comprising:
an amperometric sensor for measuring a concentration of nitrosothiols (RSNO), the amperometric sensor comprising:
an electrode located on an optical fiber, the electrode comprising:
a conducting wire wound about an outer surface of the optical fiber;
a carbon paste arranged to cover a portion of an end of the optical fiber and the conducting wire; and
an insulating film located over a portion of the carbon paste;
a nitric oxide (NO) selective permeable film located over a portion of the electrode, the electrode configured to measure an electric current generated by an oxidation reaction of nitric oxide (NO), the electrode sized to be insertable into a human body;
a light source communicating with the optical fiber;
a photocatalyst switch that controls emission of a light from the light source; and
wherein the electric current is measured by an electrochemical measurement device to determine an oxidation reaction of NO before and after a light-induced decomposition of RSNO, while the electrode is located in the human body;
wherein the nitric oxide (NO) selective permeable film is formed through a self-assembly reaction in a sol-gel process by mixing a silane monomer used to form a backbone with a perflourinated silane monomer used to give a film lipophilicity is formed on the electrode.

2. The apparatus of claim 1, wherein the electrode is formed on the optical fiber by depositing one material selected from the group consisting of platinum, gold, silver, vanadium, niobium, tantalum, indium, titanium, nickel, molybdenum, iron, copper, cobalt, chromium, bismuth, aluminum, nickel chromium and a combination thereof on an end surface of the optical fiber.

3. The apparatus claim 1, wherein the electrode is formed on the optical fiber by manufacturing one material selected from the group consisting of platinum, gold, silver, vanadium, silicon oxide, niobium, tantalum, indium, titanium, nickel, molybdenum, iron, copper, cobalt, chromium, graphite, bismuth, aluminum, zinc oxide manganese, nickel chromium and a combination thereof in a wire, rod or plate shape and attaching the material in the wire, rod or plate shape to the optical fiber.

4. The apparatus of claim 1, wherein the electrode is formed on the optical fiber by coating a mixed composition, which comprises a paraffinic oil and at least one material selected from the group consisting of gold, carbon, silver, platinum and a mixture of silver and carbon, on an end surface of the optical fiber.

5. The apparatus of claim 1, wherein the electrode is formed by coating a mixed composition, which comprises a paraffinic oil and at least one material selected from the group consisting of gold, carbon, silver, platinum and a mixture of silver and carbon, on an end surface of a cylindrical optical fiber, an operating circuit connection line is mounted on a lateral surface of the optical fiber, and a coating layer from the mixed composition is formed on a lateral surface of the optical fiber comprising the operating circuit connection line.

6. The apparatus of claim 5, wherein a coating of an insulating material is further provided over the coating layer formed on the lateral surface of the optical fiber.

7. The apparatus of claim 1, wherein the optical fiber is in a cylindrical shape having a diameter of 250 μm to 3 mm, and made of plastic, silica ($SiO_2$) or multicomponent glass.

8. The apparatus of claim 1, wherein the optical fiber is a single mode optical fiber (SMF), a multiple mode optical fiber (MMF), a step index-type (SI) optical fiber or a graded index-type (GI) optical fiber.

9. The apparatus of claim 1, wherein the photocatalyst switch configured to start and stop the light-induced decomposition of RSNO supplies and intercepts light from the light source to a dark room in which the electrode is disposed.

10. The apparatus of claim 1, wherein the light-induced decomposition is caused by light having a maximum wavelength range from an ultraviolet region (320 to 350 nm) to a visible region (550 to 590 nm).

11. The apparatus of claim 1, wherein the RSNO is at least one selected from the group consisting of S-nitrosoalbumin (Alb-NO), S-nitroso-1-cysteine (CysNO), S-nitroso-1-cysteinemethylester (CMESNO), S-nitroso-d,1-penicillamine (PSNO), S-nitroso-N-acetylcysteineamine (ACSNO), S-nitroso-N-acetyl-1-cysteine (NACysNO), S-nitrosocaptopril (SNOCAP), S-nitroso-mercaptoethylamine, S-nitroso-3-mercapto-propanoic acid, S-nitrosohomocysteine (HcysNO), S-nitroso-b,d-thioglucose, S-nitroso-N-acetyl-d,1-penicillamine (SNAP), S-nitroso-N-acetyl-d, 1-penicillaminyl glycine methyl ester and S-nitroso-1-glutathione (GSNO).

12. The apparatus of claim 1, further comprising:
a cell configured to mount the amperometric sensor;
a pump configured to transport a sample into the cell; and
a tubing configured to supply the sample into the cell or discharge the sample from the cell.

13. The apparatus of claim 12, wherein the cell comprises:
passages configured to mount a working electrode, an auxiliary electrode and a reference electrode, respectively;
a channel configured to connect the passages and allow the sample to flow in the cell; and
a connection unit connected to a tubing configured to supply the sample from the outside into the cell and discharge the sample from the cell to the outside.

14. The apparatus of claim 12, wherein the device uses a light source selected from the group consisting of a laser, a halogen lamp, a metal halide lamp, a sodium vapor light, a three-wavelength electrodeless lamp, a LED, an incandescent lamp, a fluorescent lamp and a high-frequency lamp.

* * * * *